Figure 1A:
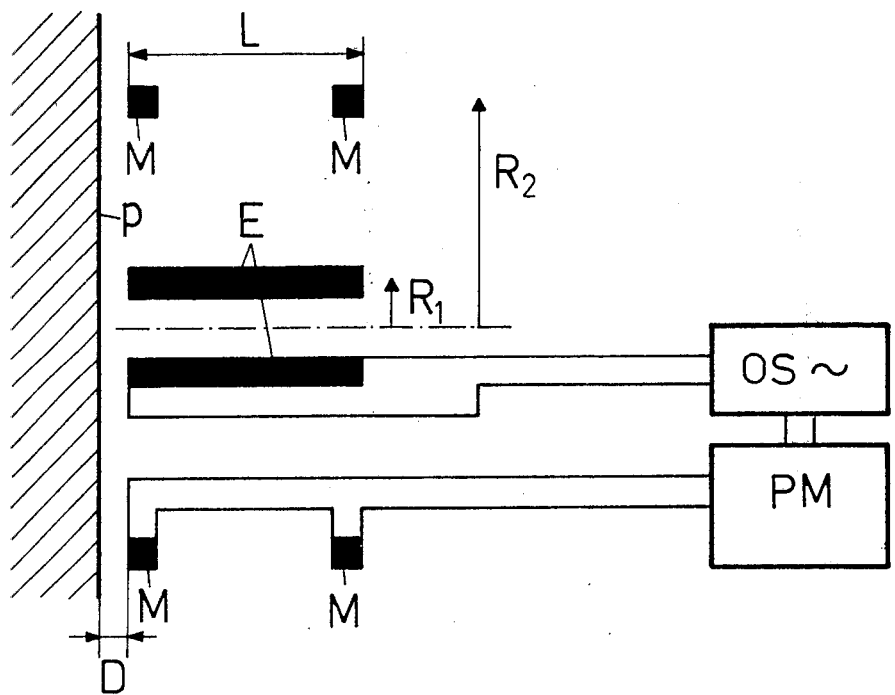

United States Patent
Brandli et al.

[11] 3,936,734
[45] Feb. 3, 1976

[54] METHOD FOR CONTACTLESS MEASUREMENT OF CONDUCTIVITY AND/OR TEMPERATURE ON METALS BY MEANS OF EDDY CURRENTS

[75] Inventors: Gerold Brandli, Windisch; Pierre Keller, Baden, both of Switzerland

[73] Assignee: BBC Brown Boveri & Company Limited, Baden, Switzerland

[22] Filed: Jan. 21, 1975

[21] Appl. No.: 542,774

[30] Foreign Application Priority Data
Feb. 6, 1974   Switzerland.......................... 1617/74

[52] U.S. Cl................................ 324/40; 73/362 R
[51] Int. Cl.$^2$......................................... G01R 33/12
[58] Field of Search............... 324/40, 34 TE, 34 R; 73/362 R, 342

[56] References Cited
UNITED STATES PATENTS
2,764,734   9/1956   Yates.................................. 324/40

OTHER PUBLICATIONS
Dodd, C.V.; A Portable Phase-Sensitive E.C. Instrument; Mat. Eval. Mar. 1968; pp. 33–36.
Dodd et al., Thickness Measurements Using E.C. Techniques; Mat. Eval. May 1973; pp. 73–84.
Dodd, C.V.; Applications of a Phase-Sensitive E.C. Instrument; Mat. Eval; June, 1964; pp. 260–262 & 272.

Primary Examiner—Robert J. Corcoran
Attorney, Agent, or Firm—Pierce, Scheffler & Parker

[57] ABSTRACT

A method for contactless measurement of conductivity and/or temperature on metals by means of the eddy current effect induced within the metal by an alternating magnetic field produced by an excitation coil fed with alternating current arranged with its axis perpendicular to the surface of the metallic test specimen, there being in addition to the excitation coil a pair of measuring coils of equal radius arranged coaxially and symmetrically with respect to the excitation coil at each end respectively of the excitation coil and having an axial length substantially less than that of the excitation coil. The two measuring coils are connected electrically in series opposition and the phase angle between the current in the measuring coils and the current in the excitation coil is taken as an indication of the measured variable. In order to reduce the so-called "lift-off" effect to a minimum and allow accurate contactless measurement such that substantial tolerances are permissible for the distance between the test specimen and measuring head which carries the coils, the radius between the excitation coil on the one hand, and the measuring coils on the other, is smaller than ¼ or greater than 4, depending on whether the measuring coils are located respectively outside or inside the excitation coil, and the measuring head is at such a distance from the specimen surface that the phase angle between the excitation-coil signal and the measuring-coil signal exhibits a maximum.

3 Claims, 3 Drawing Figures

METHOD FOR CONTACTLESS MEASUREMENT OF CONDUCTIVITY AND/OR TEMPERATURE ON METALS BY MEANS OF EDDY CURRENTS

The invention concerns a method for contactless measurement of conductivity and/or temperature on metals by means of eddy currents, whereby with the aid of an excitation coil fed with an alternating current and having its axis standing vertically on the test specimen, an alternating magnetic field is generated which penetrates into the surface of the metal and by inductive means gives rise to eddy currents, and in addition to the excitation coil there are two measuring coils of equal radius arranged coaxially and symmetrically with respect to the excitation coil, the length of each measuring coil being substantially smaller than the length of the excitation coil, such that the measuring coils are connected in series opposition and the phase angle between the current in the excitation coil and the current in the measuring coils is used as an indication of the measured variable. Methods based on the eddy-current principle for measuring conductivity and/or temperature have been known for some time. In the case of a device available commercially under the name "Sigmatest," a single test coil is used which is placed on the metal surface. The eddy currents created in the metal by the alternating magnetic field act as the loaded secondary winding of a transformer, and their effect on the test coil is to alter its electrical properties as a function of the conductivity. Attention has to be paid here to the undesirable "lift-off effect" which occurs if the sensing coil is "lifted off" the metal surface by surface roughness or intervening layers (oxide) (journal "Metall" No. 178 (1955), pages 14–22).

The influence of the lift-off effect can be reduced to a large extent by additional measures. The excitation coil has been combined with two measuring coils in differential connection. These coils are much shorter than the excitation coil and are arranged coaxially and symmetrically with respect to the latter (the measuring coils are preferably located inside the excitation in such a way that the outer end faces of the measuring coils, when viewed from the center of the complete assembly, lie on a plane with the two end faces of the excitation coils). Because the measuring coils are connected in series opposition, they do not produce a signal when there is no test specimen; if brought close to a metal object, however, the alternating magnetic field generates eddy currents in the object, and these in turn give rise to a "reflected" alternating magnetic field. This reflected magnetic field then influences the "front" measuring coil after the manner of a transformer, whereas the second measuring coil is influenced only slightly, or not at all. If the amplitude of the alternating voltage induced in the front measuring coil is used as a characteristic quantity dependent on conductivity or temperature (but also on other parameters, such as the thickness of the specimen), the influence of the "lift-off" effect is still considerable. As was found later, however, this influence is greatly reduced if the phase difference between the input signal (excitation coil) and the output signal (measuring coils) is taken as the characteristic quantity, instead of the amplitude. This technique is described, for example in the article by Dodd and Simpson "Thickness measurement using eddy current techniques" in the journal "Materials Evaluation," May 1973, p. 73–84 (here the emphasis is on measuring thickness, but other factors, including conductivity, are also discussed, though these are considered more specifically in the article by Dodd "A portable phase-sensitive eddy current instrument" in "Materials Evaluation," March 1968, p. 33–36 ).

FIG. 1a of the article by Dodd and Simpson shows not only the electrical configuration of excitation coil and measuring coils, but also the practical geometrical arrangement of the coils. According to this the measuring coils are situated coaxially inside the excitation coil, and the ratio of their radii is relatively low; the radius of the excitation coil is shown as being some 1.5 to 2 times as large as the radius of the measuring coils.

The object of the invention is to reduce further the influence of the lift-off effect and to allow contactless measurement such that substantial tolerances are permissible for the distance between test specimen and measuring head without influencing the measured value. A particular application here might be for measurements, e.g., temperature measurements, on objects of large surface area in cyclical motion, such as rotors, etc., with which certain diameter tolerances are unavoidable. It has in fact been found that when certain, hitherto disregarded, conditions concerning the arrangement and dimensions of the measuring coils are observed, the phase angle in relation to the distance measuring head/specimen passes through a maximum. If the measuring head is situated at this maximum, the dependence of phase angle on distance is very slight and the sensitivity to distance of the system is further greatly reduced beyond the reduction already achieved by using the phase angle.

This object is achieved in that the radius ratio between the excitation coil on the one hand, and the measuring coils on the other, is smaller than ¼ or greater than 4, depending on whether the measuring coils are located respectively outside or inside the excitation coil, and the measuring head is at such a distance from the specimen surface that said phase angle between the excitation-coil signal and the measuring-coil signal exhibits a maximum.

Figure 1B:
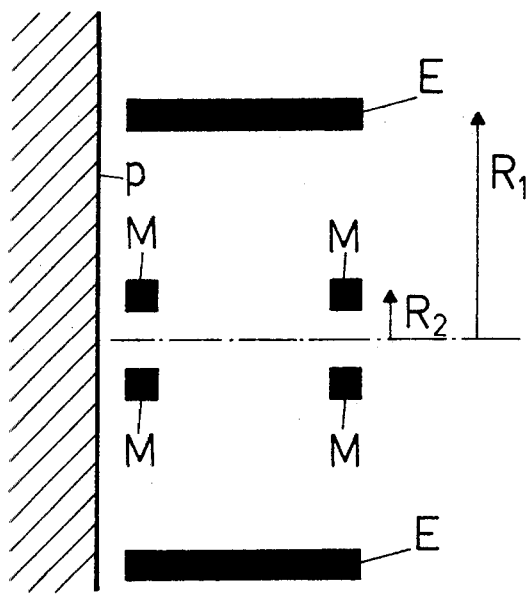

The invention will now be explained more fully with reference to the drawings. FIGS. 1a and 1b show sections through coil arrangements according to the invention, the measuring coils M being shown outside the excitation coil E in FIG. 1a, and inside coil E in FIG. 1b. The ratio $R_1/R_2$ of the mean radii of the excitation coil and measuring coils is $\leq$ ¼ in FIG. 1a, and $\geq$ 4 in FIG. 1b. The test specimen, here imagined to be a flat metal plate, is at a distance D from the front end faces of the coils (which preferably lie in one plane, as do the rear end faces). The windings of the measuring coils M are shown connected in series opposition; the resulting alternating voltage is fed to one input of a phase-angle measuring device PM, the second input of which receives the direct signal from an oscillator OS which feeds the excitation coil. L is the length of the excitation coil or the distance between the outer end faces of the measuring coils.

Figure 2:
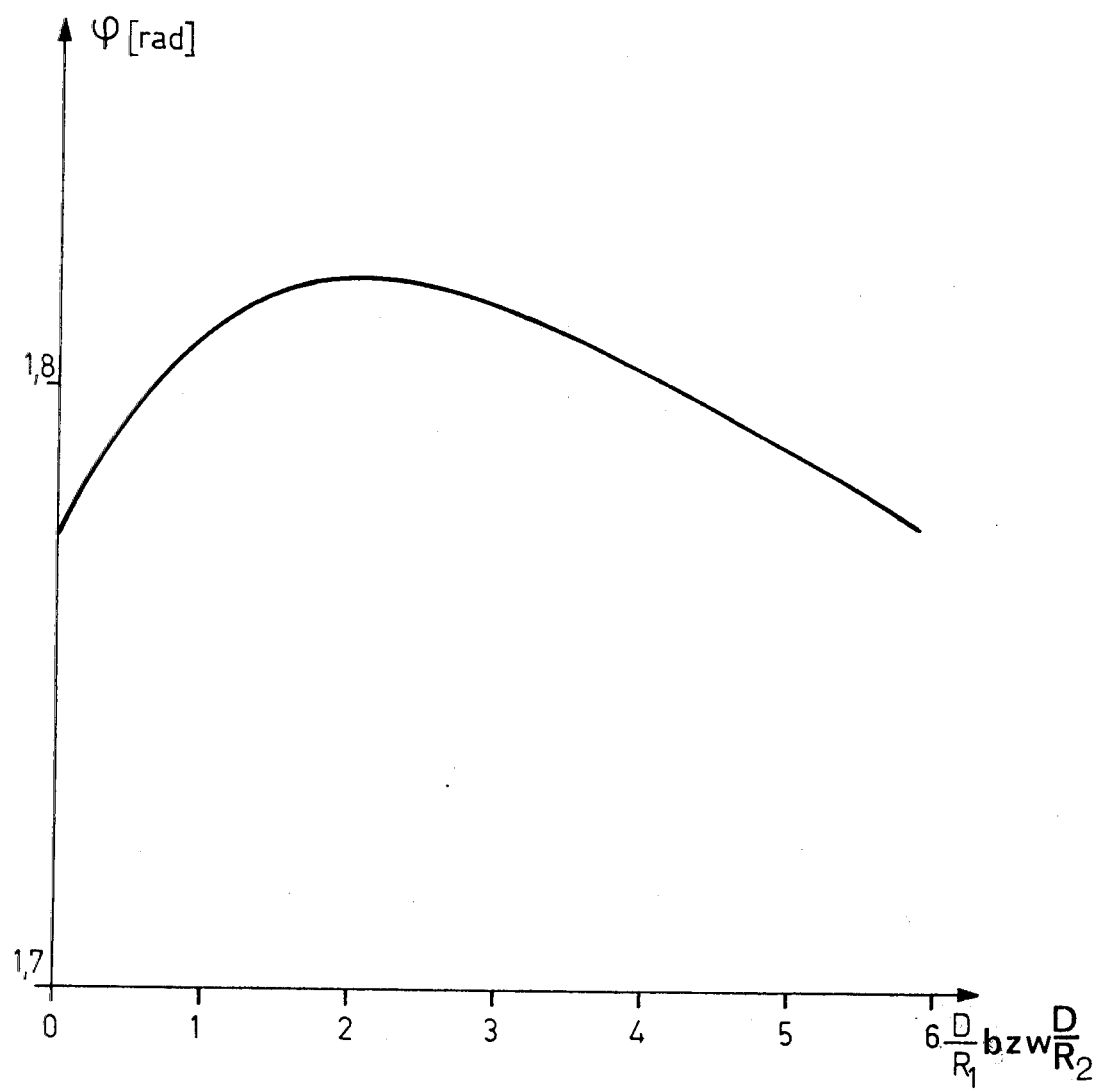

As already remarked, if the stated criteria for the relative radii of excitation coil and measuring coils are satisfied, the resultant phase angle between the primary alternating voltage and the voltage induced in the measuring coils, i.e., the signal appearing at the output of the phase-angle measuring device PM, exhibits a maximum when distance D varies. This can be seen from FIG. 2, in which the resultant phase angle $\phi$ is plotted as a function of the ratio $D/R_1$ between distance D and radius $R_1$ of the excitation coil. In the vicinity of the maximum the dependence of phase angle on distance is only slight. On the other hand, this maximum is closely related to the conductivity of the specimen, both as regards the position of this maximum (i.e., the distance from the specimen surface) and as regards its value.

The conductivity of a specimen having a plane surface, for example, can then be measured in that an indicating instrument connected to the output of the phase-angle measuring device is calibrated for a number of reference specimens of known conductivity. For this, the measuring head, fixed to a stand and able to move perpendicular to the reference surface by means of suitable guiding elements, is moved progressively towards each reference specimen in turn, preferably from a considerable distance, and the deflection of the indicating instrument is observed. When the deflection ceases to increase as the movement is continued, the maximum has been reached and the deflection corresponds to the conductivity of the reference specimen. The maxima for other reference specimens can be found in the same way and calibrated with the appropriate conductivity. Intermediate values can be interpolated.

When measuring a specimen of unknown conductivity it is necessary only to repeat this procedure, i.e., the distance from the measuring head to the specimen surface is varied progressively, starting from an appreciable distance, until the pointer ceases to move in response to further fine adjustment. If adjustment is made too far, the movement of the pointer will reverse; a slight adjustment is then made in the opposite direction until the pointer is again stationary. Since the scale is calibrated, the position of the pointer gives a direct reading of the conductivity of the specimen.

Alternatively, the procedure for measuring the conductivity of a specimen can be such that first a reference specimen of known conductivity is mounted in front of the measuring head, which is able to move in the perpendicular direction, and the measuring head is moved vertically relative to the surface of the reference specimen until the deflection of the phase-angle measuring device (PM) shows a maximum. The head is then fixed at this maximum, the phase angle is measured and the value is retrievably stored. When measuring the unknown conductivity of a specimen, the latter is set immediately in the position of the reference specimen so that the distance between specimen surface and measuring head is the same as with the reference specimen. The excitation frequency is then varied until the phase-angle measuring device PM shows the same deflection as previously with the reference specimen. In this way the phase angle maximum is obtained automatically as a function of an imaginary variation of the distance between measuring head and specimen and, as calculation will show, the ratio of the conductivities of the reference specimen and the 'unknown' specimen is inversely proportional to the ratio of the two excitation frequencies, and from this the unknown conductivity can be determined directly. Since the conductivity of the specimen is therefore inversely proportional to the frequency to be set for a given phase angle, and the proportionality constant is equal to the product of the conductivity of the reference specimen employed for the original calibration and the excitation frequency used for this purpose, the scale of the frequency meter can be calibrated permanently by the instrument manufacturer to indicate conductivity. The constant phase angle to be set by moving the measuring head could similarly be marked on the scale of the phase-angle measuring device PM by the instrument manufacturer. Through the application of electronics and control techniques it would also be possible to vary the excitation frequency automatically and to stop this adjustment, also automatically, when the prescribed phase angle is achieved (possibly by digital means through programming a counter).

The method of the invention can be used to particular advantage to measure, by way of the conductivity, the temperature of metallic, especially moving, objects. Cyclically rotating, cylindrical metal bodies, e.g., rollers, are considered particularly in this respect. For this it is of course first necessary to calibrate the indicating instrument. With the roller to be tested stationary, the measuring head is positioned some distance from the roller surface so that the extended axis of symmetry of the coils in the longitudinal direction intersects the roller axis, i.e., coincides with a produced roller radius; in this position the measuring head can be moved with the aid of suitable guidance towards or away from the roller axis, and can be fixed in any position.

The temperature at the point on the roller surface facing the measuring head is then measured by means of a contact thermometer, a thermocouple or other known means. The measuring head is then moved until the pointer of the indicating instrument of the phase-angle measuring device PM attains a maximum. The measured temperature is noted at this setting of the pointer. The roller is then brought to another temperature, e.g., heated, the temperature is measured with said means and the measuring head is adjusted until a maximum reading is obtained. This pointer position is again marked on the scale and the measured temperature noted. In general these two calibration points are sufficient in order to mark the temperature scale between them or beyond them. This scale is assumed to be linear, which is true within broad limits for the temperature response of the metal resistance. A third calibration point can of course be taken to achieve greater precision.

When the scale has been calibrated in this way, the roller is allowed to cool again to its operating temperature and this temperature is measured at a point in the manner described, by moving the measuring head until a maximum is achieved. The measuring head is fixed at this position. If the roller is now rotated, the temperature distribution over the circumference can be read directly. A particular advantage lies in the fact that unavoidable small variations in the diameter of the roller do not influence measurement because, as mentioned above, with this method the "lift-off" effect, i.e., the dependence of measurement on distance, is particularly small. During such temperature measurement, of course, the conductivity should not show any local fluctuations. Conversely, when measuring conductivity in the manner described above, the temperature must be constant; however, if the room temperature deviates from the temperature at which calibration was carried out, a correction can easily be applied to the measured values by making allowance for the measured room temperature.

A major advantage of the method described is that the piece of metal to be measured can be coated with a non-conducting layer (e.g., oxides, paper, etc.) without giving rise to falsified measurements.

We claim:

1. A method for contactless measurement of conductivity and/or temperature on metals by means of eddy currents, whereby with the aid of a measuring head including thereon an excitation coil fed with an alternating current and having its axis standing vertically on the test specimen, an alternating magnetic field is generated which penetrates into the surface of the metal and by inductive means gives rise to eddy currents, and in addition to the excitation coil there are two measuring coils of equal radius arranged coaxially and symmetrically with respect to the excitation coil, the length of each measuring coil being substantially smaller than the length of the excitation coil, the measuring coils are connected in series opposition and the phase angle between the signal in the excitation coil and signal in the measuring coils is used as an indication of the measured variable, characterized in that the radius ratio between the excitation coil on the one hand, and the measuring coils on the other, is smaller than ¼ or greater than 4, depending on whether the measuring coils are located outside or insdie the excitation coil, and the distance between the measuring head and the specimen surface is adjusted until the said phase angle between the excitation-coil signal and the measuring-coil signal exhibits a maximum.

2. A method as claimed in claim 1, in which the phase angle between the excitation-coil signal and the measuring-coil signal is measured with a measuring device which converts the phase difference at any given time into a proportional voltage and displays it on an instrument, the scale of the instrument is calibrated in such a manner that for various reference specimens of known conductivity the distance between measuring head and reference specimen is adjusted progressively until a maximum deflection of the instrument is achieved, this maximum deflection being marked on the scale and provided with the corresponding conductivity value, and in which measurement on a specimen of unknown conductivity similarly consists in progressively moving the measuring head in the direction of the specimen surface until a maximum deflection is obtained, whereupon the conductivity can be read from the calibrated scale.

3. A method as claimed in claim 1, in which in order to determine the conductivity of a specimen a reference specimen of known conductivity is first mounted in front of the measuring head, which is able to move in the perpendicular direction, and the measuring head is moved vertically relative to the surface of the reference specimen until the deflection of a phase-angle measuring device shows a maximum, the head is fixed at this maximum, the phase angle is measured and the value is retrievably stored, and in which when measuring the unknown conductivity of a specimen this is set immediately in the position of the reference specimen so that the distance between specimen surface and measuring head is the same as with the reference specimen, and the excitation frequency is varied until the phase-angle measuring device shows the same deflection as previously with the reference specimen, the phase angle maximum being obtained automatically as a function of an imaginary variation of the distance between measuring head and specimen and the ratio of the conductivities of the reference speciman and the 'unknown' specimen being inversely proportional to the ratio of the two excitation frequencies, from which the unknown conductivity can be determined directly.

* * * * *